United States Patent [19]

Burchiel et al.

[11] Patent Number: 4,478,815

[45] Date of Patent: Oct. 23, 1984

[54] COMPOSITION AND METHOD FOR DETECTING CANCER WITH TECHNETIUM LABELED ANTIBODY FRAGMENTS

[75] Inventors: Scott W. Burchiel; Buck A. Rhodes, both of Albuquerque, N. Mex.; David R. Crockford, Haverhill, Mass.

[73] Assignees: Nuc-Med, Inc., Albuquerque, N. Mex.; University Patents, Inc., Norwalk, Conn.

[21] Appl. No.: 269,404

[22] Filed: Jun. 2, 1981

Related U.S. Application Data

[63] Continuation-in-part of Ser. No. 89,153, Oct. 29, 1979, Pat. No. 4,311,688.

[51] Int. Cl.³ .................. A61K 43/00; A61K 49/00
[52] U.S. Cl. ............................. 424/1.1; 424/9; 252/645
[58] Field of Search ................. 424/1, 9, 1.5

[56] References Cited

U.S. PATENT DOCUMENTS

| | | | |
|---|---|---|---|
| 4,311,688 | 1/1982 | Burchiel et al. | 424/1.5 X |
| 4,323,546 | 4/1982 | Crockford et al. | 424/1.5 X |
| 4,331,647 | 5/1982 | Goldenberg | 424/1 |
| 4,348,376 | 9/1982 | Goldenberg | 424/1 |

*Primary Examiner*—Christine M. Nucker
*Attorney, Agent, or Firm*—Paul J. Cook

[57] ABSTRACT

F(ab')$_2$ or Fab fragments of antibodies to: (a) human chorionic gonadotropin (hCG), hCG alpha subunit, hCG beta subunit, or an hCG-like material; or (b) other tumor specific or tumor associated molecules, to include carcinoembryonic antigen (CEA), alpha fetoprotein (AFP), human melanoma associated antigens, human sarcoma associated antigens or other antigens, are radiolabeled with technetium-99m (Tc-99m). When the F(ab')$_2$ or Fab fragments of antibody to such tumor associated antigens are injected intravenously into a patient, the radiolabeled composition accumulates at tumor sites. The accumulation of the cancer seeking radiopharmaceutical at tumor sites permits detection by external gamma scintigraphy. Thus, the composition is useful in the monitoring, localization and detection of cancer in the body.

In an alternative composition, a double antibody approach to tumor localization using radiolabeled F(ab')$_2$ or Fab fragments is utilized. In this approach, a tumor specific antibody in the form of IgG, F(ab')$_2$ or Fab is first administered to a patient intravenously. Following a sufficient period of time, a second antibody in the form of F(ab')$_2$ or Fab is administered. The second antibody is radiolabeled with Tc-99m and has the property that it is reactive with the first antibody. This double antibody method has the advantage over a single antibody approach in that smaller tumors can be localized and detected and that the total amount of radioactive trace localized at the cancer site is increased.

13 Claims, 2 Drawing Figures

COMPOSITION AND METHOD FOR DETECTING CANCER WITH TECHNETIUM LABELED ANTIBODY FRAGMENTS

REFERENCE TO RELATED APPLICATIONS

This application is a continuation-in-part of application Ser. No. 089,153, filed Oct. 29, 1979, now U.S. Pat. No. 4,311,688.

BACKGROUND OF THE INVENTION

This invention relates to compositions and methods capable of detecting cancer cells or malignant tumors in humans. More particularly, this invention relates to compositions radio-labeled with Tc-99m which, when administered to a human, will accumulate at tumor sites producing a) human chorionic gonadotropin (hCG), hCG alpha subunit, hCG beta subunit or an hCG-like material or b) any other tumor associated antigen to which an antibody molecule can be prepared to include carcinoembryonic antigen (CEA) or the like.

The use of compositions which emit radiation at levels which can be detected after administration to the human body are well known. These compositions are utilized to visualize and/or monitor the functioning of various parts of the body or are used diagnostically to determine the absence or presence of particular tissue damage or disease. In one particular aspect of the prior art, radiolabeled antibodies are utilized to detect tumors having associated therewith carcinoembryonic antigen (CEA). As disclosed in U.S. Pats. Nos. 3,663,684, 3,867,363 and 3,927,193, $I^{131}$ or $I^{125}$ labeled antibodies to CEA are utilized to detect tumors which produce or are associated with CEA.

It is also well known that protein molecules can be tagged with Tc-99m in order to form diagnostic agents. An example of such a composition is Tc-99m labeled human serum albumin. The use of chelating agents for the radiolabeling of protein molecules with transition metals such as In-111 and/or Tc-99m has also been described (Meares et al, Proc. Nat. Acad. Sci., U.S.A., Vol. 11, pp 3803–3806, 1976). In addition, the use of a chelating agent for the radiolabeling of antibodies and antibody fragments including F (ab')$_2$ and Fab fragments reactive with human myosin has been described as potentially useful for imaging of myocardial infarction (Khaw and Haber, "Radioimmunochemical imaging of myocardial infarction: Utilization of anticardiac myosin antibodies." In: Tumor Imaging: The Radioimmunochemical Detection of Cancer, Ed. Burchiel, S.W., et al, U.S.A. (New York) in press.)

It has also been proposed to tag the antibody with peroxidase (McManus et al., Cancer Research, 36. pp. 2367–3481, September, 1976) in order to localize the antigen in malignant tumors in vitro. Furthermore, it has been proposed to label the IgG antibody to hCG with radioactive iodine in order to localize the antigen in human choriocarcinomas transplanted in hamster cheek pouches (Quinones et al, 1971, Journal of Nuclear Medicine, Vol. 12, pp. 69–75.) Also, it is known to utilize anti-hCG labeled with tritium or iodine to test for cancer in a human using an in vitro diagnostic test, (U.S. Pat. No. 4,116,776, Dalbow et al.)

Recently, it has been found that neoplastic tissues produce and/or express on their surface chorionic gonadotropin, chorionic gonadotropin-like material, compounds similar to and/or identical to the alpha-chain or beta-chain of chorionic gonadotropin or mixtures thereof, specifically to the degree where it is considered a more general marker than either carcinoembryonic antigen (CEA) or alphafetoprotein (AFP), (Acevedo et al., "Detection and Prevention of Cancer", Part 2, Vol. I, H. E. Nieburgs (ED) Marcel Dekker, Inc., New York, 1978, pp. 937–979). The positive identification of chorionic gonadotropin in a heterogenous group of cancer cells and its non-detection in non-cancer cells in vitro has suggested to these authors that the compound is a common antigen (common denominator) of every cell with oncogenic properties.

While radiolabeled IgG antibodies are useful for localizing tumors in vivo, when a radioisotope of sufficient half-life is present, the IgG antibodies comprise the immunoglobulins which tend to stay in the blood stream for many hours following intravenous administration. This increases the difficulty in imaging the tumor within a reasonable time period, since blood levels of the labeled IgG antibodies maintain a relatively high background activity. In nuclear medicine, a high ratio of target (tumor) to background emission is desired to obtain an image of sufficient quality to permit detection. With short-lived radioisotopes, such as Tc99m (6 hour half-life), it becomes difficult to image without the use of sophisticated background subtraction techniques (Goldenberg et al., New Eng. J. Med., Vol. 298, pp 1384–1388, 1978).

In previous published studies, it has also been shown that radioiodinated IgG antibodies specific to digoxin have a prolonged half-life in the blood stream of rabbits and baboons compared to radioiodinated Fab fragments of the same antibody (Smith et al, Clin. Exp. Immunol., 36, 384–396, 1979). In these experiments, Fab fragments of anti-digoxin antibodies were tested to determine whether the antibody fragments had a different biodistribution pattern than the whole IgG molecule following intravenous administration, and whether the Fab fragments were less toxic than IgG.

SUMMARY OF THE INVENTION

In accordance with this invention, radio-labeled compositions are provided which comprise: (1) antibody fragments (F(ab')$_2$ or Fab) to hCG, hCG alpha subunit, hCG beta subunit, or an hCG-like material, or to any other tumor associated molecule to which an antibody can be made including a human melanoma associated antigen, CEA, AFP or the like; and (2) antibody fragments (F(ab')$_2$ and Fab) to antibodies reactive with tumor associated antigens (such as hCG, hCG alpha subunit, hCG beta subunit, and hCG-like material, or other tumor associated molecules) that are labeled with Tc-99m. When using the compositions of this invention to diagnose cancer cells in a patient, therefore, the treatment can be either one of two procedures. In the first procedure (single antibody method), the patient is administered the Tc-99m labeled antibody fragment (F(ab')$_2$ or Fab fraction) to the tumor associated antigen. In the second procedure (multiple antibody method), the patient is first administered the antibody to the tumor associated antigen (IgG, F(ab')$_2$ or Fab fraction). After a sufficient period of time for the first antibody to accumulate at tumor sites which comprise the tumor associated antigen and for the unbound antibody to clear from the general circulation, the Tc-99m labeled second antibody fragment (either an F(ab')$_2$ or Fab fraction) is administered intravenously. The second antibody has the property that it is reactive with the first antibody. The biodistribution of the labeled composition is monitored by external gamma scintigraphy in order to locate cancer cells or malignant tumors. The present invention provides substantial advantages over the prior art since the compositions provide for higher sensitivity in detecting cancer cells or malignant tumors of the prior art, the technique can be performed in vivo, and the compositions are more effective in providing imaging contrast between the tumor or cancer cells and the blood system so that good imaging can be obtained quickly.

DESCRIPTION OF SPECIFIC EMBODIMENTS

Figure 1:
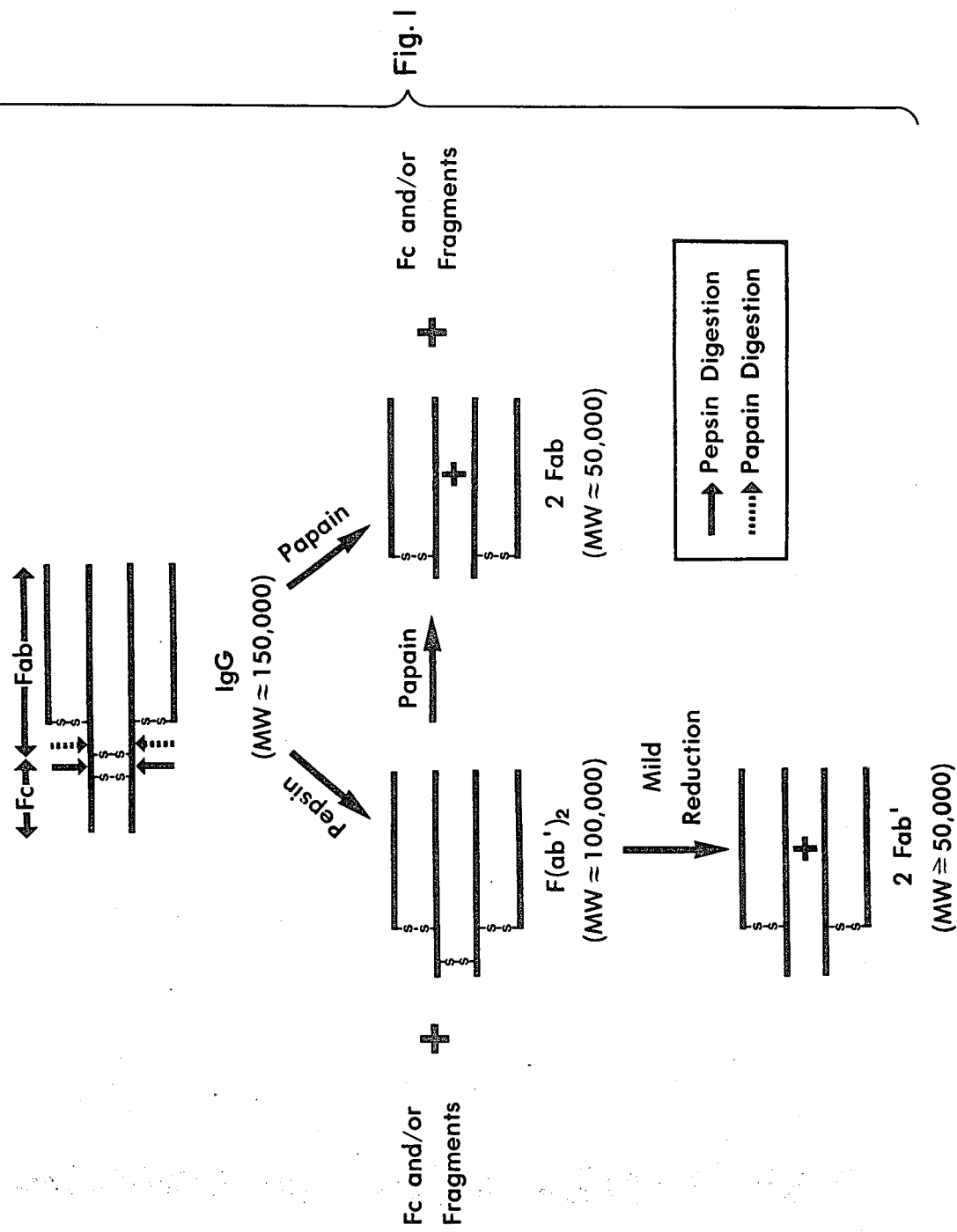

The term "antibody fragment", as used herein means $F(ab')_2$ or Fab fragments. The antibody fragments are prepared by any conventional techniques such as is shown in Example I.

Human chorionic gonadotropin (hCG) is a molecule believed to have a molecular weight ranging from about 35,000 to 38,000. HCG is found in the urine and sera of pregnant women, in patients with trophoblastic and other tumors, in the normal placenta, and is produced by certain cell cultures. HCG consists of two noncovalently boded alpha and beta chains having approximate molecular weights of 14,700 and 23,000 respectively. The alpha and beta chains can be easily dissociated; however, it has been shown that each chain is biologically inactive as a separate entity. The amino acid sequence of the alpha chain has been shown to have close similarity to the alpha chain of luteinizing hormone (hLH), follicle stimulating hormone (hFSH), and thyroid stimulating hormone (hTSH). The beta chain has similarity only to the beta chains of luteinizing hormone and less homology to those of follicle stimulating hormone and thyroid stimulating hormone. The beta chain is immunologically active in both the intact hormone and as a separate entity. Approximately 30 percent of the molecule is carbohydrate which is constituted by six different monosaccharides: sialic acid, L-fructose, D-galactose, D-mannose, N-acetylglucosamine and N-acetyl-galactosamine.

The antibody fragment last administered is labeled with technetium-99m affords improved images by scintigraphy. In contrast to iodine-labeled antibodies, technetium-99m is retained by the antibody by a chelation mechanism. Thus, the reagent is formed under reducing conditions in order to minimize or prevent the reversible reaction by which the technetium-99m becomes free of the antibody fragment. The source of the technetium-99m preferably is water soluble such as the alkali to alkaline earth metal pertechnetate. The technetium can be obtained as sodium pertechnetate Tc-99m from a conventional 99Mo/99mTc generator. Any source of pharmaceutically acceptable technetium-99m may be utilized in the present invention.

Anti-hCG, anti-hCG-beta, anti-hCG-alpha or other anti-tumor antigen antibodies are obtained by any conventional method such as by immunizing animals such as rabbits, sheep, goats or other suitable species with a suitable immunogen in order to induce production of the antibody. Serum then is harvested from the immunized animals and the specific immunoglobulins then can be obtained in sufficiently pure from such as by affinity chromatography, immunoprecipitation, nonimmune precipitation or the like. In affinity chromatography, for example, an hCG-rich fraction first is isolated such as from pregnant female serum or urine by conventional nonimmune preciptation or immunoprecipitation techniques followed by chromatography on DEAE-cellulose followed by gel filtration on Sephadex G-100 or by another suitable purification technique. The hCG-rich fraction thus obtained is passed onto a column of a cyanogen halide activated or periodate activated gel such as Sephadex, Sepharose or cellulose or another insoluble polysaccharide with carboxyl, polyhydroxyl or N-hydroxylsuccinimide ester functionality in order to chemically attach the hCG by a weak covalent bond to the gel. The serum obtained from the animal then is passed through the column and the anti-hCG, anti-hCG-beta or anti-hCG-alpha becomes specifically attached to the hCG or hCG subunits which comprise the corresponding antigen in the column while the remainder of the other immunoglobulins (non-hCG specific antibodies) pass through the column. The anti-hCG, anti-hCG-beta or anti-hCG-alpha then is recovered from the column by passing an appropriate buffer, e.g., ammonium hydroxide solution through the column in order to break the weak covalent bond between the antibody and the hCG-gel matrix. The antibody can be obtained in any conventional manner such as by elution with solution or buffer of appropriate ionic strength and pH. $F(ab')_2$ or Fab fragments then can be produced from the antibody.

In the multiple antibody technique, after the antibody to the tumor associated antigen is isolated, the antibody, hereinafter referred to as a second antibody, is produced in an animal species other than the species used to produce the antibody to the tumor associated antigen, hereinafter referred to as the first antibody. Either of the two procedures described below may be utilized for antibody preparation.

(1) An animal of a species different from the species in which the first antibody was produced is immunized with a nonimmune IgG fraction (normal IgG) of immunoglobulin from an animal species used to obtaining the first antibody in order to produce a desired second antibody which binds to the first antibody or;

(2) Immune IgG fraction (anti-tumor associated antigen) from the animal used to produce the first antibody is administered to an animal of a different species to produce a desired second antibody which binds to its first antibody.

The process for obtaining the composition of this invention is illustrated by the following schematic route:

EMBODIMENT 1

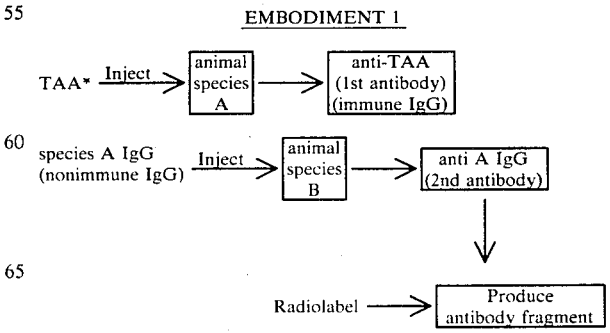

EMBODIMENT 2

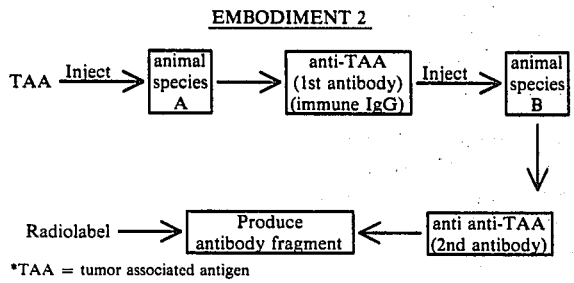

*TAA = tumor associated antigen

It is to be understood that animal species A is not a human. It is preferred to utilize Embodiment 1 because the second antibody produced therefrom will bind specifically to any immune IgG which immunogen (antigen) came from the animal species used to produce the immune IgG. Serum containing second antibody then is harvested and the second antibody is obtained in purified form as for example by the procedures set forth above for the anti-hCG or anti-hCG-beta.

It is to understood that the method of forming the antibodies is not critical to the present invention so long as they are in sufficiently pure form as to render the composition immunoreactive for their respective antigens. An alternative method for forming the antibodies useful in the present invention comprises the method for making antibody producing hybridomas disclosed by Kohler and Milstein (1975), Nature, Vol. 256, pp. 495–497.

It is to be understood also that while the multiple antibody embodiment of the present invention is described above with respect to the use of two antibodies in series, the present invention is not limited to a series of only two antibodies, the second of which is radiolabeled. In order to provide higher concentrations of the radioisotope located on the tumorous cell, a series of three or more antibodies may be utilized, the fragment of the last of which is radio-labeled. By operating in this manner, the number of available sites associated with the tumorous cell for attachment of the radio-labeled antibody is increased greatly. The series of suitable antibodies is made as described above, with the only restrictions being that the antibodies adjacent in the series are produced from animal species different from the next adjacent antibodies in the series and that the first antibody produced in the series is anti-hCG, anti-hCG-beta, or any other antibody to a tumor associated. These procedures are shown schematically as Embodiments 3 and 4.

EMBODIMENT 3

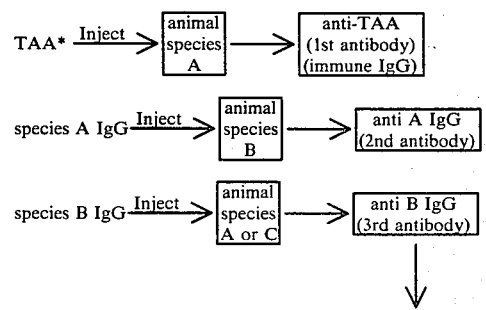

—continued
EMBODIMENT 3

Radiolabel ⟶ Produce antibody fragment

EMBODIMENT 4

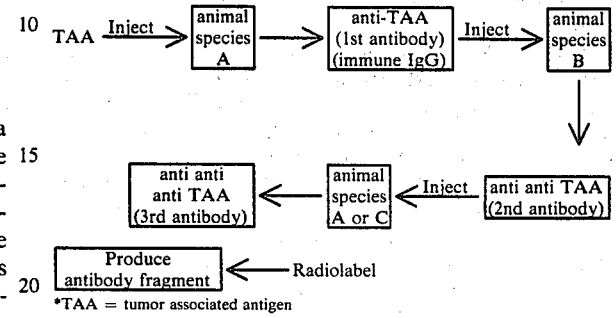

*TAA = tumor associated antigen

The antibodies are administered parenterally to the patient in the same sequence as they are produced with the radiolabeled antibody fragment being administered last. That is, the first antibody obtained as described above is administered first. Subsequently, the second antibody is administered. The last antibody fragment in the series of antibodies is radiolabeled and will be referred to as the "last antibody fragment". The primary limitation on the number of antibodies that are administered is the possibility that the patient will experience undesirable side reactions to the antibodies. The possibility of undesirable side reactions occurring may be reduced by the use of antibody fragments obtained by conventional techniques.

The technetium-99m labeled antibody fragment is prepared by acidic, basic or neutral (ligand exchange) radiolabeling techniques. In one particular and preferred aspect of this invention, the technetium-labeled antibody fragment is obtained by a ligand exchange process. In this process, a solution of technetium (IV) is prepared by mixing a solution of technetium such as in the form of a pertechnetate ($TcO_4^-$) and saline with a stannous reducing solution, e.g., stannous fluoride-acetate having a pH between about 3 and 5.5. In this procedure, the stannous ions reduce technetium (VII) to technetium (IV). The reduced technetium-99m first is chelated onto the top of a column of Sephadex G-25 (dextran cross-linked with carboxyl functionality) by passing the aqueous solution of technetium-99m through the column. The solution has a pH between about 5.5 and 7.0. The column then is washed with saline to essentially remove free pertechnetate ($TcO_4^-$) or unusual species of technetium thereby leaving the technetium-99m chelated or absorbed or otherwise bound to the column. A physiologic solution of the antibody fragment then is prepared with appropriate buffer so that the resultant solution has a pH between about 6 and 9, preferably between about 7 to 8. When operating within this pH range, denaturation of the antibody fragment is eliminated or minimized. The antibody fragment is then added in a minimum volume to the top of the column where the technetium-99m/Stannous complex is bound and where it is allowed to stand until the technetium-99m is bound to the antibody fragment having stronger bonding sites than the column material. This usually occurs within about 30 minutes. The column then is washed to remove the labeled antibody fragment. Washing can be efected with a known volume of human serum albumin diluted with 50/50 ACD (acidified citrated Dextrose) or the like followed by a known volume of saline. In this manner, the volume of washing saline solution containing the labeled antibody fragment can be determined and the labeled antibody will remain on the column or will be eluted at a rate different from that of the labeled, immunologically intact, antibody fragment.

A second preferred method for forming technetium-99m labeled antibody fragment comprises direct labeling of the fragment or pretinned fragments. In this method, a buffered solution is admixed with an acidic solution of $SnCl_2$ which is a reducing agent for pertechnetate. The buffered solution can comprise sodium and/or potassium phthalate, tartrate, gentisate, acetate, borate or mixtures thereof havng a pH of between 4.5 and 8.0, preferably about 5.5. Tartrate is utilized to maintain the appropriate concentration of stannous ion in solution to effect the desired solution pH. The $SnCl_2$ preferably is added to the buffer as a solution with concentrated HCl. Thereafter, the solution is neutralized such as with sodium hydroxide to attain a pH of between about 4.5 and 8.0, preferably about 5.5. The antibody fragment then is added to the neutralized solution in an amount to attain a concentration of protein fragment up to just less than that which would begin to precipitate the protein fragment in the buffer being used. In order to attain the desired degree of protein fragment labeling, the resultant stannous ion, buffer, protein fragment solution is allowed to incubate. For example, at room temperature, the incubation time should be at least about 15 hours, preferably at least about 20 hours under a nitrogen or an inert gas atmosphere. If desired, this solution can be heated moderately to reduce the incubation time. The solution then can be either freeze-dried and subsequently reconstituted for admixture with pertechnetate or can be admixed directly with pertechnetate solution to obtain the labeled fragment. If desired, the resultant radiolabeled protein fragment may be further purified to separate the labeled protein fragment from free technetium such as by chromatography in a Sephadex column. However, this last step is optional.

The present invention also provides a kit with which a user can prepare the composition of this invention and administer it to a patient relatively quickly after preparation. The kit includes each antibody or antibody fragment either in lyophilized form, frozen or liquid of suitable ionic strength and pH, and either containing or not containing a reducing agent. If without the reducing agent, the last administered antibody fragment can be admixed with a reducing solution or solid provided within the kit and in a separate container. Representative, suitable reducing agents are $SnCl_2$ or $SnF_2$ to be dissolved or already dissolved in an appropriate solution, such as sodium acetate/acetic acid, acidified deionized or distilled water, or the like, such that a reducing pH of about 3 to 8.0 is obtained when combined with technetium-99m as sodium pertechnetate. Therefore, technetium-99m as pertechnetate is either reduced in the presence of reducing agent prior to addition of the last to be administered antibody fragment or is reduced when added to the last to be administered antibody fragment containing reducing agent. The solution of labeled antibody fragment is then suitable for administration to a patient.

In an alternative embodiment, the eluted labeled protein fragments can be admixed with a dilute solution of human serum albumen, e.g., 1% and passed through a bed of anion exchange resin in order to remove free pertechnetate from the labeled protein fragment thereby purifying the labeled final antibody so that the preparation is substantially free of radiochemical contamination. If desired, these anion exchange resins need not be a part of the columns untilized for labeling but can comprise a separate bed through which the labeled protein fragment is passed.

In an alternative embodiment of this invention, the kit can include a column of material which entraps or otherwise binds technetium-99m such as Sephadex, Sepharose or cellulose. The column of this material also can contain the reducing agent for technetium or the reducing agent can be added thereto when it is desired to reduce the technetium.

The labeled final antibody fragment is administered by intravenous injection in a pharmaceutically acceptable saline solutin, sterile and pyrogen-free. Suitable dosages are usually between about 0.5 and 30 millicuries, preferably between about 10 and 20 millicuries of technetium-99m final antibody fragment for the normal 70 kg patient. The patient then can be scanned by conventional scintigraphy within 1 hour to about 5 days after administration of the labeled protein. Tumors are located in those areas showing a high concentration of labeled final antibody.

It should be understood that the procedure of this invention also can be based upon antigens other than hCG or hCG-beta which are tumor specific such as carcinoembryonic antigens, alpha fetoprotein antigens, human melanoma associated antigens, human sacranoma associated antigens, or other tumor specific markers wherein one or a series of antibodies are produced as described above and the last produced antibody fragment is radiolabeled.

The following examples illustrate the present invention and are not intended to limit the same.

EXAMPLE I

FIG. 1 is a schematic diagram of a typical method for making antibody fragments.

This example illustrates the preparation of F(ab')$_2$ and Fab fragments of normal rabbit IgG. The preparation of antibody fragments of IgG is illustrated in FIG. 1. Rabbit IgG was obtained from Cappel Laboratories (Cochranville, PA). The IgG antibody was dissolved in phosphate buffered saline at a concentration of 10 mg/ml, and was titrated to a pH of 4.0 with glacial acetic acid. Pepsin was obtained from Worthington Biochemicals (Millipore Corporation, Freehold, NJ), and was added to the IgG antibody solution at a substrate ratio of 3 mg enzyme per 100 mg of IgG. The mixture was incubated at 37° C. for 4 hours. After removing any formed precipitate via centrifugation, the solution was placed on a Sephadex (Pharmacia, Piscatway, NJ) G-150 column that was 1.6×100 cm. Three peaks of protein were eluted from this column: Peak I corresponded to the F(ab')$_2$ fragment, as determined by molecular weight sizing and immunoreactivity studies showing an absence of an Fc portion of the molecule; peaks II and III were found to contain antibody fragments that did not possess immunoreactivity. The F(ab')$_2$ fractions were pooled and were concentrated by negative pressure dialysis to a concentration of approximately 2 mg/ml. The concentrated F(ab')$_2$ fractions were then exposed to papain obtained from Boehringer Mannheim (Indianapolis, IN) in the presence of 2 mM EDTA and 10 mM cysteine-HCl for 24 hours at 37° C. The F(ab')$_2$ to papain ratio was 3 mg per 100 mg enzyme. Following this incubation/digest, the solution was again placed on a G-150 Sephadex column of 1.6×100 cm size, with two peaks of protein being eluted. The first peak corresponded to undigested F(ab')$_2$, while the second peak corresponded to the Fab fraction. The purity of the Fab fraction was determined by polyacrylamide electrophoresis. In an alternative method, rabbit fragments were prepared from rabbit F(ab')$_2$ by a mild reduction with 5 mM dithiothreitol for 1 hour at room temperature. The reduction reaction was stopped by the addition of 250 mM iodoacetamide. The resultant Fab' was dialyzed extensively against 0.9% sodium chloride, and was concentrated via negative pressure dialysis.

EXAMPLE II

This example illustrates a direct method of labeling of pre-tinned antibody fragments, such as those obtained by the procedures outlined in Example I. Technetium-99m is obtained from New England Nuclear (Boston, MA).

To 0.4 ml of 50 mM sodium-potassium tartrate buffer pH 5.5 (10.51 g/l) is added 1.6 ml of a 50 mM potassium biphthalate buffer pH 5.5 (10.21 g/l adjusted with 10 N NaOH). To the resultant buffer solution is added 0.02 ml of 0.5 M SnCl$_2$-HCl (94.8 g/l conc HCl). The resultant solution is titrated back to a pH of 5.65±0.05 by adding thereto 0.02 ml of 10 N NaOH plus additional amounts of 1 N NaOH required to obtain the specified pH. To this solution is added 0.3 ml of a saline solution of the antibody to anti-hCG (10 mg protein/ml 0.9% saline). The reaction vessel is allowed to stand approximately 21 hours at room temperature under a nitrogen atmosphere. This solution may be freeze-dried to make a Tc-99m labeling kit. Thereafter, 0.5 ml of NaTcO$_4$ with an activity of 0.001 to 50 mCi is added to the fragment containing composition and allowed to stand for one half to one hour to effect substantially complete labeling of the fragment prior to use. The resultant product is diluted with 1.0 ml of 1% human serum albumin in 0.9% NaCl and then is passed through a Sephadex (Pharmacia, Piscataway, NJ) G-25 column pretreated with stannous biphthalate to remove free Tc-99m from the labeled product.

EXAMPLE III

This example illustrates that Fab fragments which have been radiolabeled with Tc-99m using the pre-tinning method outlined in Example II retain their immunoreactivity, and that the Tc-99m is incorporated into the complex that forms when a Tc-99m labeled Fab fragment of an antibody combines with its antigen. In this example, the antibody Fab fragment and the other protein reagents were obtained from Cappel Laboratories (Cochranville, PA). The antigen that was used was human IgG (HuIgG), which was labeled with I-125 using a standard chloramine T and sodium metabisulfide method. The antibody Fab fragment tested in this system was a Fab fragment of sheep anti-human IgG. Rabbit anti-sheep IgG was used to precipitate immune complexes. Thus, a double label radioimmunoassay was employed to test the immunoreactivity of Tc-99m labeled Fab fragments.

Figure 2:
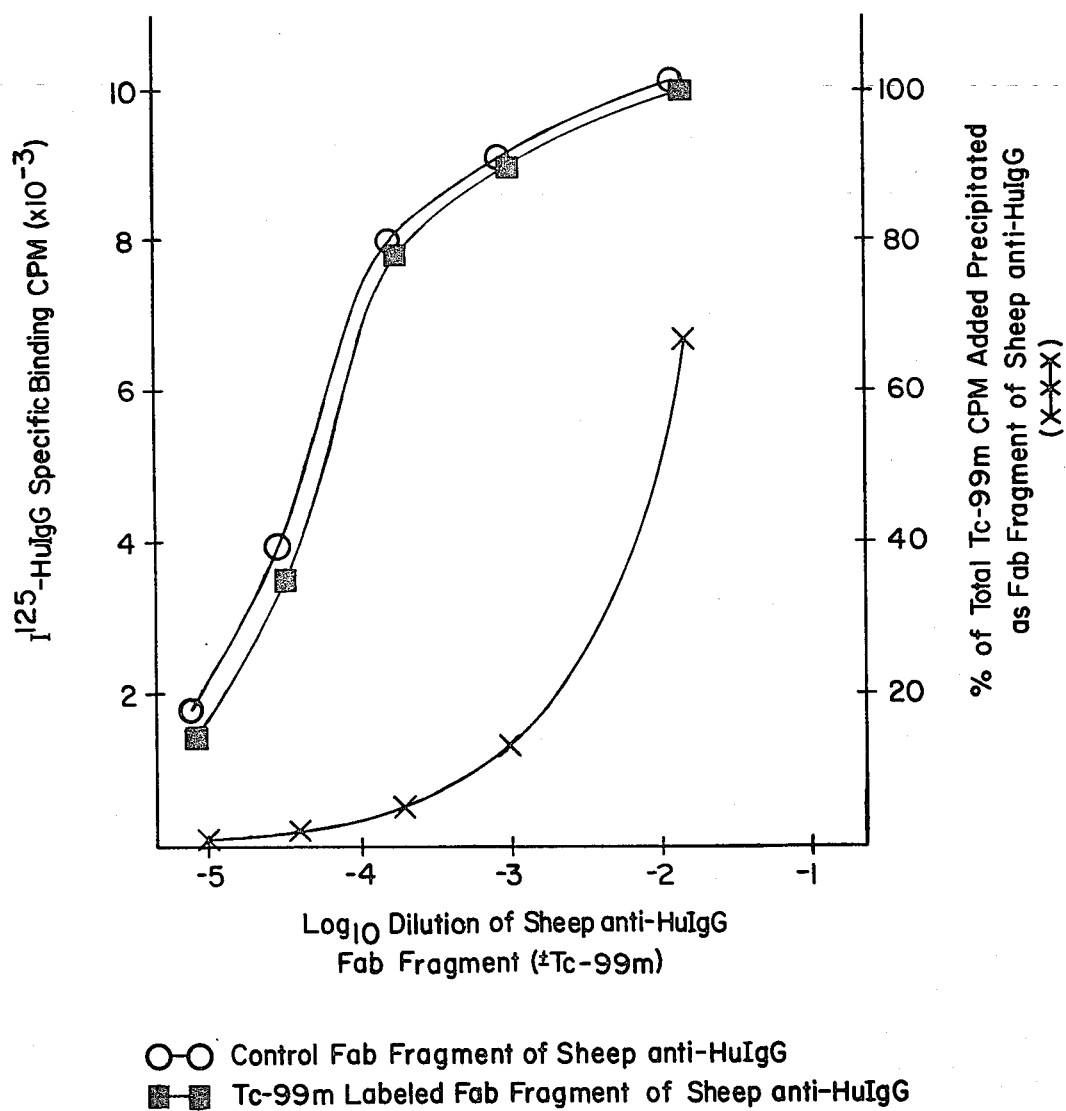

FIG. 2 shows that the radioimmunotitration curves obtained with control Fab's (those that were not radiolabeled with Tc-99m) and Tc-99m labeled Fab's are essentially identical. This illustrates that the Tc-99m labeling does not alter the immunoreactivity of the Fab fragment. The figure also shows that Tc-99m is incorporated into the precipitated immune complex. Thus, Tc-99m labeled Fab's must be reacting with the I-125 labeled antigen.

EXAMPLE IV

This example illustrates that F(ab')$_2$ fragments prepared according to the methods outlined in Example I are capable of binding to immobilized antigen. The antigen in this example is highly purified human chorionic gonadotropin (hCG) obtained from Serono Laboratories, Inc. (Rome, Italy). This hCG is coupled to cyanogen bromide activated Sepharose 4B obtained from Sigma Chemical Company (St. Louis, MO). Highly purified antibodies to hCG were obtained from Serono Laboratories (Rome, Italy) and F(ab')$_2$ fragments of anti-hCG were prepared according to Example I. The purified F(ab')$_2$ fragments of anti-hCG were radiolabeled with I-125 using a standard chloramine T-sodium metabisulfide iodination reaction. The I-125 labeled F(ab')$_2$ anti-hCG fragments were then incubated with the hCG-Sepharose (approximately 1 mg of hCG per ml of Sepharose beads) in a phosphate buffered saline solution (PBS) containing 1% human serum albumin (HSA) at 37° C. for 20 minutes in a siliconized glass test tube. The mixture was then washed three times with the PBS-HSA buffer to remove all unbound I-125 F(ab')$_2$ fragments. The beads were then counted to determine the percentage of total counts added that were bound to the hCG-Sepharose. Non-immune sheep IgG was included as a control for nonspecific binding to the hCG-Sepharose. Specific binding to hCG was determined by eluting the bound antibody from the beads using 3 ml of 1 M pH 3.2 guanidine. After a 20 minute incubation with this elution buffer at 37° C., the hCG-Sepharose was washed by centrifugation with this buffer. The beads were then counted for residual activity, with the amount of counts eluted being considered specific binding, less the amount of CPM of the I-125 labeled non-immune IgG eluted with guanidine. The results of this experiment are shown in Table I. The results of this experiment showed that I-125 labeled F(ab')$_2$ fragments prepared by the methods outlined in Example I retain their immunoreactivity with hCG.

TABLE I

BINDING OF I-125 LABELED ANTI-hCG F(ab')$_2$ FRAGMENTS TO hCG-SEPHAROSE

| Sample* | Percentage of Total CPM Added Specifically Bound to hCG-Sepharose |
|---|---|
| 100 ng of non-immune sheep IgG (negative control) | 1.4% |
| 100 ng of sheep anti-hCG IgG (positive control) | 53.4% |
| 100 ng of sheep anti-hCG F(ab')$_2$ | 60.5% |
| 50 ng of sheep anti-hCG F(ab')$_2$ | 53.6% |
| 25 ng of sheep anti-hCG F(ab')$_2$ | 60.0% |
| 12.5 ng of sheep anti-hCG F(ab')$_2$ | 57.1% |
| 6.25 ng of sheep anti-hCG F(ab')$_2$ | 66.7% |
| 3.13 ng of sheep anti-hCG F(ab')$_2$ | 57.1% |
| Average % of all F(ab')$_2$ Test Samples | 60.0 ± 3.6% |

*All antibodies were labeled with I-125 using a standard chloramine T-sodium metabisulfide method

EXAMPLE V

This example illustrates that antibody fragments, Fab and F(ab')$_2$, are cleared faster than are the whole antibodies whether labeled with radioiodine or with Tc99m. A faster blood clearance is essential for a Tc99m labeled radiopharmaceutical because of the short half-life of the Tc99m. The whole antibodies to hCG were obtained as in Example IV. The F(ab')$_2$ were obtained as in Example I. The Tc99m labeled whole antibodies and antibody fragments were prepared as in Example II. The purified F(ab')$_2$ fragments of anti-hCG and the whole antibodies were radiolabeled with I-125 using a standard chloramine T-sodium metabisulfide iodination reaction. The radiolabeled antibodies or antibody fragments were injected via the tail veins of female Swiss Webster mice. The animals were subsequently sacrificed, dissected and the distribution of the antibodies and fragment in the various tissues was determined by measuring the radioactivity in individual tissue samples using a gamma scintillation counter. Data presented in Tables II and III show that the fragments are cleared from the blood more rapidly than are the whole antibodies.

TABLE II

BLOOD LEVELS OF Tc$^{99m}$-LABELED ANTIBODY FOLLOWING I.V. INJECTION INTO SWISS MICE[1]

| | % Injected Dose/Organ[2] | | |
|---|---|---|---|
| Time (hrs.) | IgG | F(ab')$_2$ | Fab |
| 1 | 50 | ND[3] | 12 |
| 2 | 45 | ND | 10 |
| 5 | 33 | ND | 7 |
| 24 | 15 | ND | 3 |
| 72 | 7 | ND | 1 |

[1]Values obtained after injection of approximately 100 μg of protein.
[2]Percentages are from a representative experiment and are ± 15%.
[3]Not determined.

TABLE III

BLOOD LEVELS OF I$^{125}$-LABELED ANTIBODY FOLLOWING I.V. INJECTION INTO SWISS MICE[1]

| | % Injected Dose/Organ[2] | | |
|---|---|---|---|
| Time (hrs.) | IgG | F(ab')$_2$ | Fab |
| 1 | 75 | 25 | 25 |
| 2 | 65 | 17 | 12 |
| 5 | 45 | 10 | 10 |
| 24 | 30 | 4 | 4 |
| 72 | 20 | 2 | 2 |

[1]As in Table II.
[2]Percentages are ± 15% of the actual value used to calculate percentage.

We claim:

1. A composition of matter comprising a radiolabeled antibody fragment, said radiolabeled antibody fragment being reactive with a second antibody or second antibody fragment which is directly reactive with a tumor specific antigen, said reactivity with said second antibody, or second antibody fragment either being direct or through a series of at least one third antibody or third antibody fragment, the last of said series being directly reactive with said second antibody or antibody fragment, said radiolabel consisting of technetium-99m.

2. The composition of claim 1 wherein said second antibody is anti-human chorionic gonadotropin.

3. The composition of claim 1 wherein said second antibody is anti-human chorionic gonadotropin-beta.

4. The composition of any one of claims 1, 2 or 3 wherein said radiolabeled antibody fragment is directly reactive with said antigen.

5. The process of detecting cancer cells and/or a malignant tumor in a human which comprises injecting into the human an antibody or fragment thereof against a tumor specific antigen, subsequently injecting into the human the second antibody or fragment thereof or the series of antibodies or fragments thereof of claim 1 in the sequence said antibodies are produced with the last of said injected antibodies being said radiolabeled antibody fragment, the time between injections being sufficient to allow substantially all of said antigen and said antibody or fragments thereof not bound to said cells and/or tumor to be metabolized and monitoring the biodistribution of the radiolabeled antibody fragment in said human.

6. The process of claim 5 wherein said second antibody is anti-human chorionic gonadotropin.

7. The process of claim 5 wherein said second antibody is anti-human chorionic gonadotropin-beta.

8. A diagnostic kit suitable for forming a composition useful in identifying a cancer cell and/or a malignant tumor which comprises a sterile package containing an antibody fragment being reactive with a second antibody or second antibody fragment which is directly reactive with said a tumor specific antigen, said reactivity with said second antibody or second antibody fragment either being direct or through a series of at least one third antibody or third antibody fragment, and means for mixing the contents of said sterile package with reduced technetium-99m in a physiologically acceptable aqueous solution.

9. The kit of claim 8 wherein a physiologically acceptable reducing agent useful in resucing technetium (VII) to the technetium (IV) state is admixed with said antibody fragment.

10. The kit of claim 8 wherein said antibody fragment in said sterile package is lyophilized.

11. The kit of claim 9 wherein said antibody fragment and reducing agent are lyophilized.

12. The kit of claim 8 which includes a column of material capable of binding technetium in the IV state and of releasing said technetium when contacted with a solution of said antibody fragment.

13. The kit of claim 8 which includes an ion exchange resin capable of selectively removing pertechnetate ion from a solution containing pertechnetate from a protein labeled with technetium-99m.

* * * * *